United States Patent

Hähn et al.

[11] Patent Number: 6,133,497
[45] Date of Patent: Oct. 17, 2000

[54] CATALYST FOR REMOVING OLEFINS FROM AROMATIC COMPOUNDS OR MIXTURES THEREOF

[75] Inventors: Reinhard Hähn, Vilsheim; Thomas Engelhardt, Freising; Uwe Flessner, Munich; Werner Zschau, Steinebach, all of Germany

[73] Assignee: Sud-Chemie A.G., Germany

[21] Appl. No.: 08/930,473

[22] PCT Filed: Mar. 26, 1996

[86] PCT No.: PCT/EP96/01320

§ 371 Date: Jan. 7, 1998

§ 102(e) Date: Jan. 7, 1998

[87] PCT Pub. No.: WO96/30119

PCT Pub. Date: Oct. 3, 1996

[30] Foreign Application Priority Data

Mar. 31, 1995 [DE] Germany ............... 195 12 134

[51] Int. Cl.[7] ............... C07C 7/12; C07C 2/02; B01J 20/12; B01J 21/16
[52] U.S. Cl. ............ 585/820; 585/823; 585/532; 585/533; 502/80; 502/81; 502/85; 502/408; 502/410
[58] Field of Search ................... 585/820, 823, 585/829, 520, 532, 533; 502/80, 81, 85, 408, 410

[56] References Cited

U.S. PATENT DOCUMENTS

| | | | |
|---|---|---|---|
| 3,835,037 | 9/1974 | Fairweather et al. | 208/260 |
| 4,193,454 | 3/1980 | Goldstein | 166/302 |
| 4,208,268 | 6/1980 | Sato et al. | 208/46 |
| 4,531,014 | 7/1985 | Gregory et al. | 585/415 |
| 4,795,550 | 1/1989 | Sachtler et al. | 208/307 |
| 5,053,569 | 10/1991 | Marquis et al. | 585/255 |
| 5,180,864 | 1/1993 | Sanderson et al. | 585/10 |
| 5,749,955 | 5/1998 | Shaked et al. | 106/287.17 |

FOREIGN PATENT DOCUMENTS

| | | |
|---|---|---|
| 0 116 469 | 8/1984 | European Pat. Off. . |
| 0 449 453 | 10/1991 | European Pat. Off. . |
| 2385789 | 10/1978 | France . |
| 2599275 | 12/1987 | France . |
| 1094389 | 12/1960 | Germany . |
| 3728812 | 10/1988 | Germany . |
| 1162945 | 9/1969 | United Kingdom . |

*Primary Examiner*—Walter D. Griffin
*Attorney, Agent, or Firm*—Scott R. Cox

[57] ABSTRACT

A catalyst is described on the basis of acid-activated smectitic clay minerals for removing olefins from aromatic compounds or mixtures of aromatic compounds which is characterized in that the acid-activated clay mineral contains at least 5 milli-equivalents/100 g of exchangeable $Al^{3+}$ cations.

25 Claims, 1 Drawing Sheet

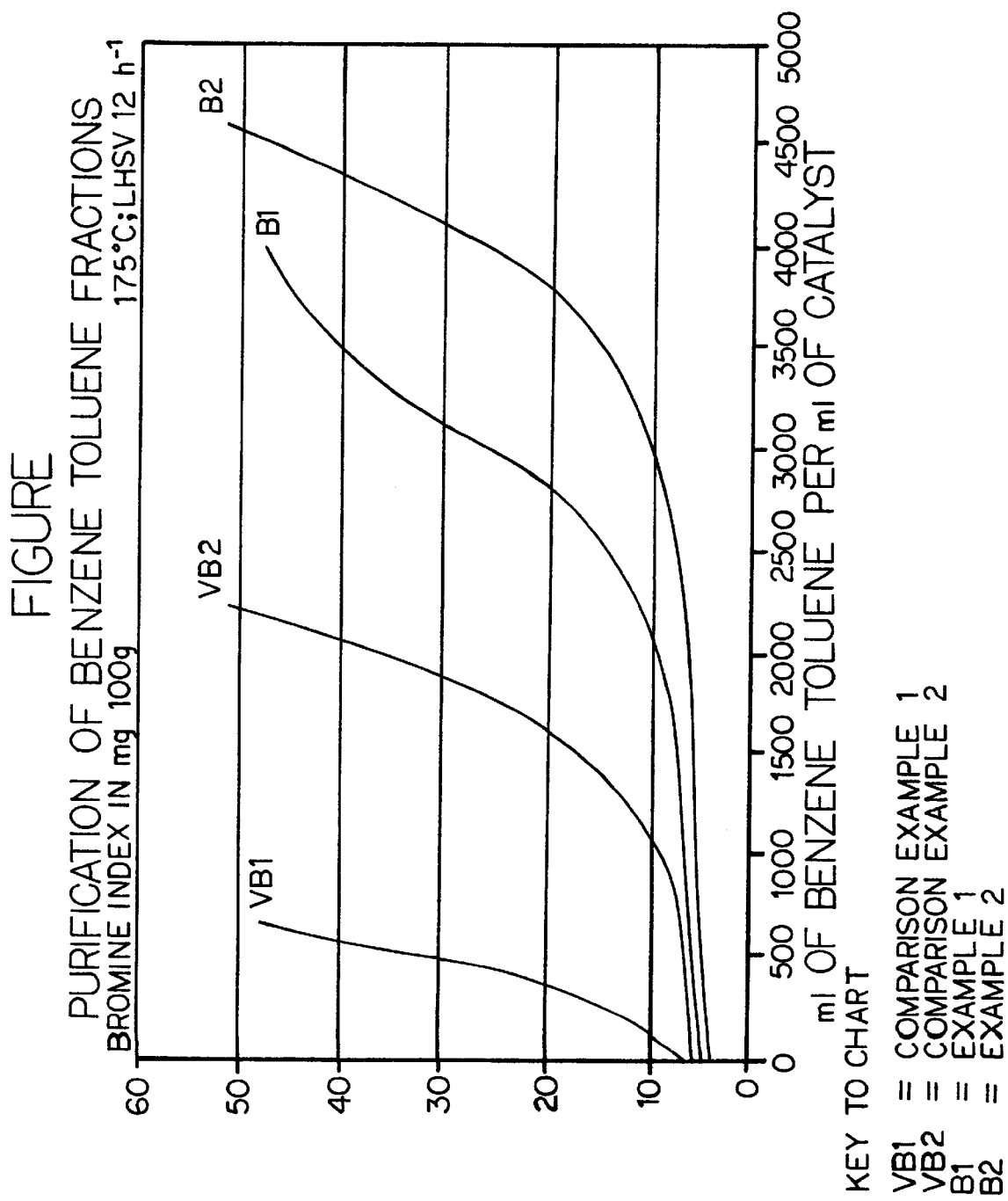

CATALYST FOR REMOVING OLEFINS FROM AROMATIC COMPOUNDS OR MIXTURES THEREOF

SPECIFICATION

The invention pertains to a catalyst for removing olefins from aromatic compounds or mixtures of aromatic compounds.

Benzene, toluene and the xylenes (BTX), the most important industrial aromatic compounds, are manufactured virtually exclusively nowadays via the catalytic or thermal conversion of suitable mineral oil fractions.

In the case of so-called catalytic reforming, a paraffinic naphtha fraction is treated at approximately 400° C. with catalysts that have been coated with a noble metal. Aromatic compounds are formed from the saturated hydrocarbons during this catalytic process. These aromatic compounds are then separated from the non-aromatic compounds by means of extraction or, as the case may be, crystallization and then they are processed further by distillation.

The sulfolane process (Ullmann's Encyclopadie der Technischen Chemie, Volume 8 (1974), page 395) has gained acceptance as the most important process for the extraction-based separation of benzene/toluene mixtures.

In addition to the desired aromatic compounds, small quantities of olefins are also formed during catalytic reforming. These olefins, whose concentration lies below 1% as a rule, interfere with further processing and have to be removed. Since the undesired olefins have approximately the same boiling points as the aromatic compounds, separation by means of distillation is not possible.

Catalytic treatment with alkaline earth aluminum silicates, e.g. activated smectites in granular form, has gained acceptance on a world wide basis as an economical process for the removal of these olefins. In this connection, the stream of aromatic compounds is fed through a solid bed reactor at approximately 150–200° C. The granular materials act as a catalyst in this way; the undesired olefins are transformed into higher boiling products which can then be separated with ease by means of distillation.

It is known that natural or synthetic alkaline earth aluminum silicates are used preferentially as catalysts which are suitable for the removal of olefins. Thus the most widely different processes have been described using acid-activated bentonites (bleaching earths). In this connection, reference may be made, for example, to GB-1 162 945 and DE-C-22 36 996. The commercial products for the purification of aromatic compounds are generally granulated acid-activated bentonites in the form in which they are used for refining edible oils. As a rule, the products are supplied in a grain size range between 0.3 and 0.6 mm; their specific surface area varies between 200 and 400 m²/g; their ion exchange capacity (IEC) varies between 30 and 60 milli-equivalents/100 g.

In addition to the acid-activated bentonites, that are preferably used, use can also be made of synthetic silicates such as Al silicates, Mg silicates and Zr silicates.

The use of zeolites for the removal of olefins from fractions of aromatic compounds is described in U.S. Pat. No. 4,795,550. Zeolites are certainly very reactive but the formation of polymeric by-products takes place in their narrow system of pores and this leads to very rapid deactivation of the catalyst bed.

The working life of acid-activated bentonites in fixed bed reactors varies very markedly depending on the process conditions and lies between several weeks and a year. After this, so much catalytic activity has been lost as a result of deactivation processes that exchange of the catalyst is necessary. The process operators of such aromatic plants are therefore interested in a highly active catalyst which excels by virtue of a long working life.

The task of the present invention is to develop catalysts for removing olefins from aromatic compounds or mixtures of aromatic compounds on the basis of smectites with a constant, high catalytic activity and thus a long working life.

The subject of the invention is thus a catalyst based on acid-activated smectitic clay minerals for removing olefins from aromatic compounds or mixtures of aromatic compounds which is characterized by the feature that the acid-activated clay mineral contains at least 5 milli-equivalents/100 g of exchangeable $Al^{3+}$ cations.

BRIEF DESCRIPTION OF THE DRAWING

The Figure shows the results of the performance of Comparison Examples 1 and 2 and Examples 1 and 2.

Bentonite is used as the starting material for the acid-activated smectitic clay mineral, whereby its primary mineral is montmorillonite. However, other smectitic clay minerals, such as beidellite, saponite, glauconite, nontronite and hectorite, can also be used.

The catalyst is preferably characterized by
(a) a specific surface area of approximately 50 to 500 m²/g;
(b) an ion exchange capacity (IEC) for exchangeable cations of, in total, approximately 20 to 60 milli-equivalents/100 g, whereby the proportion of $Al^{3+}$ ions in terms of the IEC amounts to approximately 10 to 60 milli-equivalents/100 g; the proportion of alkali metal ions in terms of the IEC amounts to less than approximately 7.0 milli-equivalents/100 g and the proportion of alkaline earth ions in terms of the IEC amounts to less than approximately 50 milli-equivalents/100 g;
(c) a total acidity of more than approximately 10 mg of KOH/g;
(d) a proportion of free alkaline earth ions or alkali metal ions of less than 5 milli-equivalents/100 g;
(e) a quantity of free silicic acid of approximately 15 to 55% by weight.

The concentration of exchangeable $Al^{3+}$ ions preferably amounts to approximately 10 to 50 milli-equivalents/100 g.

The term "exchanaeable $Al^{3+}$ ions" is to be understood to mean $Al^{3+}$ ions which are bound at sites between layers and not inside the layers of the smectitic clay mineral. They are chemically bound as a result of ion exchange so that they cannot be washed out with water. The concentration of exchangeable $Al^{3+}$ ions is determined within the context of the measurement of the total ion exchange capacity (IEC). In this connection, a sample of the catalyst (2 g) is boiled for one hour under reflux in 100 ml of a 2 normal $NH_4Cl$ solution and then it is allowed to stand for a further 16 hours at room temperature. The sample is then filtered off and washed until it is free from chloride. The total IEC is then determined by measuring the $NH_4^+$ ions which have become incorporated into the lattice by exchange. For this purpose, the concentration of ammonium ions in the $NH_4^+$-exchanged catalyst is determined using the Kjeldahl method. The concentration of exchangeable $Al^{3+}$ ions in the filtrate of the boiled $NH_4Cl$ solution is determined spectrophotometrically and expressed in milli-equivalents per 100 g of catalyst. The concentrations of alkali metal ions and alkaline earth ions in the filtrate of the boiled $NH_4Cl$ solution are determined in the same way.

The total IEC and the proportion of exchangeable cations in the acid-activated smectitic starting material are determined using the same method.

In addition to exchangeable $Al^{3+}$ ions, the catalyst in accordance with the invention can also contain free $Al^{3+}$ ions on the surface, in the pores and in the volume between the grains. These $Al^{3+}$ ions can be removed by simple washing of the catalyst with water.

For this purpose, a sample of the catalyst (10 g) is washed 5 times with, in each case, 100 ml of water at 25° C. in a filter prior to boiling with the $NH_4Cl$ solution until aluminum can no longer be detected in the last quantity of wash water. The aluminum is again determined spectrophotometrically in the combined wash waters. The other free cations can also be determined in the same way.

The determination of the IEC and the proportion of the individual ions in terms of the total IEC as well as the determination of the free cations can also be carried out in smectitic starting materials that have not been acid-treated. In this connection, an excessively high concentration of exchangeable calcium or magnesium ions is simulated by the result. This is caused by the feature that the smectitic starting material is frequently contaminated with calcium carbonate and/or magnesium carbonate which is dissolved on boiling with the $NH_4Cl$ solution.

It is assumed that both the exchangeable $Al^{3+}$ ions and the free $Al^{3+}$ ions exert their catalytic action in the form of Lewis acids. Until now, Lewis acids (particularly aluminum chloride) have been used only in homogeneous catalysis. It is therefore surprising that the exchangeably bound $Al^{3+}$ ions also act in the form of Lewis acids in the heterogeneous catalysts in accordance with the invention. It is especially surprising that the catalytic effect of the exchangeable $Al^{3+}$ cations is more marked than the catalytic effect of the free $Al^{3+}$ ions.

The catalysts in accordance with the invention are preferably present in the form of particles with a size of more than 0.1 mm and these are termed "granular materials" below. Molded objects, such as extruded materials, spheres, pellets, etc. are also included among these. These molded objects can in general be up to approximately 10 mm in size.

The subject of the invention is also a process for the manufacture of a catalyst which is characterized in that one treats an acid-activated smectitic starting material with an aluminum salt solution whose quantity is designed in such a way that the concentration of exchangeable $Al^{3+}$ ions is increased to at least 10 milli-equivalents/100 g and that a proportion of free $Al^{3+}$ ions is optionally present as well.

In this connection, one generally starts out from an acid-activated smectitic starting material with a concentration of exchangeable $Al^{3+}$ ions of less than 5 milli-equivalents/100 g, although one can also start out from a material with a higher concentration of exchangeable $Al^{3+}$ ions. The catalytic activity of such a starting material, that already fulfills the conditions for a catalyst in accordance with the invention, can be increased further as a result of the exchange of additional $Al^{3+}$ ions. The treatment in accordance with the invention can therefore be carried out in two or more stages.

In the first preferred variant of the process in accordance with the invention, one proceeds in such a way that use is made of the aluminum salt in a 1 to 5-fold molar excess and that exchange of the $Al^{3+}$ ions takes place for monovalent and divalent cations and the catalyst is then washed in order to remove free, i.e. water-soluble aluminum salts as well as the salts of the monovalent and divalent cations in the event that these interfere with the total process.

In this connection, a suspension of the smectitic clay material (bleaching earth suspension) is impregnated with an aluminum salt solution, especially an aluminum sulfate solution, whereby direct ion exchange takes place. After exchange for several hours at room temperature or an elevated temperature, the excess of aluminum ions is washed out after which the exchanged bleaching earth product is then dried. The granulation process follows.

In accordance with the second variant, one can spray a previously size-classified granulated material comprising an acid-activated bentonite (granulated bleaching earth) with an excess of an aqueous aluminum sulfate solution, whereby part of the $Al^{3+}$ ions is bound in an exchangeable manner and another part of the $Al^{3+}$ ions is present in free form, i.e. merely adsorbed. After spraying, the material is dried at approximately 80 to 150° C. or, preferably, at approximately 100° C.

In both variants, a few percent of the aluminum salt are adequate in order to achieve considerably increased catalytic activity. Various aluminum salts are basically suitable. Aluminum sulfate is preferable to aluminum chloride for commercial and technical reasons.

One can transform the catalyst, which has been enriched with $Al^{3+}$ ions, into a granulated material with a particle size of >0.1 mm in accordance with both variants.

The subject of the invention is also the use of the catalyst in accordance with the invention for removing olefins from aromatic compounds or mixtures of aromatic compounds.

The additional characteristic features, which are indicated in the claims and in the specification, are measured as follows:

1. Specific surface area: in accordance with the BET method (single point method using nitrogen in accordance with DIN 66131, whereby the sample has been de-gassed for 10 hours at 150° C. beforehand).

2. Total acidity: a sample of the catalyst (5 g) is suspended in 250 ml of a 5 wt. percent NaCl solution at 95° C. and then filtered; the clear filtrate, which is obtained, is titrated with 0.1 n KOH solution using phenolphthalein [as the indicator]. The total acidity is expressed in mg of KOH/100 g of catalyst.

3. Free silicic acid: during the acid-activation of smectitic clay minerals, the exchangeable cations in the interstitial positions are first replaced by protons after which the cations, which are bound in the octahedral layer, are dissolved out at the edges of the packets of layers and amorphous silicic acid remains behind. The proportion of this amorphous (free) silicic acid increases with increasing intensity of the acid activation process (concentration, temperature, pressure and time). The free silicic acid can be determined by boiling a sample (1 g) of the acid-activated bentonite in 100 ml of 2% $Na_2CO_3$ solution for 10 minutes. Soluble sodium silicate is formed from the free silicic acid, whereas the silicon, which is bound in the lattice, is not dissolved out. The free silicic acid, which has gone into solution, can then be determined in any desired manner after filtration, e.g. using the sodium molybdate method.

The invention will be elucidated in a non-limitative manner by the examples below.

COMPARISON EXAMPLE 1

Preparation of a granulated material comprising non-treated bentonite 100 kg of dried Bavarian calcium bentonite (Tonsil® 13 from the Süd-Chemie AG firm) with the properties which were indicated in Table 1 are ground and mixed for 10 minutes with 32 kg of water in a Drais Intensive Mixer and then extruded in a single screw extruder to give 2 mm thick strands.

The moist strands were dried for 10 hours at 110° C. and then reduced in size in a roller fragmenter with a gap separation of 1 mm. The fraction between 0.3 mm and 0.6 mm was then sieved off.

COMPARISON EXAMPLE 2

Preparation of a non-modified granulated bleaching earth material 100 g of bleaching earth in the form of bentonite, which had been activated by hydrochloric acid (Tonsil® Optimum FF from the Süd-Chemie AG firm) with the properties which were indicated in Table 1 are mixed for 10 minutes with 40 kg of water in a Drais Intensive Mixer and then extruded in a single screw extruder to give 2 mm thick strands.

The moist strands were treated further as in Comparison Example 1.

EXAMPLE 1

Impregnation of acid-activated bentonite with aluminum sulfate 100 kg of the bleaching earth granulated material from Comparison Example 2 were introduced into a pellet-making dish and were then sprayed with 20 liters of 25% aluminum sulfate solution. The impregnated granulated material was dried for 24 hours at 120° C.

The $Al^{3+}$ ions were partially introduced into the lattice by exchange; in part, they were also located on the surface of the material. The properties of the impregnated, granulated material are given in Table 1.

EXAMPLE 2

(Introduction of $Al^{3+}$ ions by exchange into acid-activated bentonite)

100 kg of the acid-activated bentonite from Comparison Example 2 were dispersed in 500 liters of distilled water using vigorous stirring. After a time of stirring of 3 hours, 20 kg of aluminum sulfate were added in solid form and then stirred for a further 12 hours at room temperature.

The suspension, which contains aluminum sulfate, then had water removed from it on a filter press; it was washed after this with 1,000 liters of demineralized water. The moist filter cake was dried for 12 hours at 120° C.

The dried filter cake was then reduced in size in a fragmenter and the fraction between 0.3 and 0.6 mm was sieved off. The properties of the catalyst, which were obtained in this way, are given in Table 1.

USAGE EXAMPLE (Determination of the catalytic activity of the catalysts for removing olefins from mixtures of aromatic compounds)

A mixture of aromatic compounds (70% by weight of benzene and 30% by weight of toluene), which was obtained by sulfolane extraction, with an olefin proportion which corresponds to a bromine index of 50 mg $Br_2/100$ g (in accordance with ASTM D 1491) was fed over an HPLC column by means of an HPLC pump, whereby the catalyst, which was to be investigated, was located in the column in the form of a charge (reactor volume 10 ml). The HPLC column was located in a thermostat which was capable of being regulated and in which the temperature is held constant at 200° C. In order to avoid gas formation at these high temperatures, a back-pressure regulator was located between the HPLC column and the electronically controlled sampling valves. A counter-pressure of 50 bar was set up at this back-pressure regulator.

A LHSV (liquid hourly space velocity=liquid space velocity) of 12 $h^{-1}$ was set up with the help of the HPLC pump. A sample of the purified mixture of aromatic compounds was removed every 24 hours from the time-controlled sampling valve and the bromine index was determined.

In order to evaluate the catalytic activity, the bromine index was plotted against the operating time (days). The results are given in the appended Figure.

Accordingly the acid-activated bentonite in accordance with Comparison Example 2 had a longer working life than the non-treated bentonite in accordance with Comparison Example 1. However, the catalyst in accordance with Example 2 had the longest working life, whereby this catalyst contains only exchangeable $Al^{3+}$ ions. The catalyst in accordance with Example 1 had a somewhat shorter working life and also contains free $Al^{3+}$ ions in addition to the exchangeable $Al^{3+}$ ions. It is found from this that the effect in accordance with the invention is most pronounced when the $Al^{3+}$ ions are bound, in an exchangeable manner, at the sites between the layers of the acid-activated bentonite.

TABLE I

| Catalyst | BET surface area ($m^2/g$) | ion exchange capacity (IEC) milli-equivalents/100 g | | | | | | | free $Al^{3+}$ in the catalyst (meq/100 g) | acidity (mgKOH/g) | free $SiO_2$ (%) |
| --- | --- | --- | --- | --- | --- | --- | --- | --- | --- | --- | --- |
| | | Total | $Al^{3+}$ | $Fe^{3+}$ | $Ca^{2+}$ | $Mg^{2+}$ | $K^+$ | $Na^+$ | | | |
| Comparison Example 1 | 70 | 63.7 | 0.2 | 6.5 | 38.0 | 44.0 | 3.5 | 1.5 | <0.1 | 0 | 0.3 |
| Comparison Example 2 | 237 | 31.7 | 8.0 | 2.9 | 16.3 | 2.4 | 1.1 | 0.9 | <0.1 | 8.7 | 32.4 |
| Example 1 | 220 | 59.3 | 38.9 | 3.4 | 4.3 | 2.4 | 1.0 | 0.5 | 24.7 | 43 | 28.4 |
| Example 2 | 232 | 30.6 | 18.1 | 2.1 | 5.5 | 1.0 | 0.3 | 1.7 | 0.4 | 26 | 33.8 |

What is claimed is:

1. A catalyst for removing olefins from aromatic compounds or mixtures of aromatic compounds comprising an acid-activated clay mineral comprising exchangeable $Al^{3+}$ ions, wherein the proportion of exchangeable $Al^{3+}$ ions is at least about 5 milli-equivalents/100 g of the catalyst, wherein the acid-activated clay mineral is formed into particles having a specific surface area from approximately 50 to about 250 m²/g.

2. The catalyst of claim 1 wherein the acid-activated clay mineral comprises at least about 20 to about 60 meq./100 g $Al^{3+}$ ions.

3. The catalyst of claim 1 wherein the acid-activated clay mineral further comprises exchangeable alkali metal ions contributing less than about 7.0 meq./100 g to the ion exchange capacity of the catalyst.

4. The catalyst of claim 1 wherein the acid-activated clay mineral further comprises alkaline earth metal ions contributing less than about 50 meq./100 g to the ion exchange capacity of the catalyst.

5. The catalyst of claim 1 wherein the acid-activated clay mineral has a total acidity of more than about 15 mg of KOH/g of the clay mineral.

6. The catalyst of claim 1 wherein the acid-activated clay mineral further comprises free alkaline earth metal ions or alkali metal ions in a proportion of less than about 5 meq./100 g of the catalyst.

7. The catalyst of claim 1 wherein the acid-activated clay mineral further comprises about 15 to about 55 percent by weight silicic acid.

8. The catalyst of claim 1 wherein the acid-activated clay mineral further comprises free $Al^{3+}$ ions.

9. The catalyst of claim 8 wherein the free $Al^{3+}$ ions are present on the surface, within the pores or in the intermediate particle volumes of the acid-activated clay mineral.

10. The catalyst of claim 1 wherein the acid-activated clay mineral is formed into particles with diameters greater than about 0.1 mm.

11. A catalyst for removing olefins from aromatic compounds or mixtures of aromatic compounds comprising an acid-activated clay mineral comprising $Al^{3+}$ ions, alkali metal ions and alkaline earth metal ions, wherein the ion exchange capacity of the acid activated clay mineral is about 20 to about 60 meq./100 g of the catalyst, wherein the acid-activated clay mineral is formed into particles having a specific surface area from approximately 50 to about 250 m²/g.

12. The catalyst of claim 11 wherein the alkali metal ions contribute less than about 7.0 meq./100 g to the ion exchange capacity of the catalyst.

13. The catalyst of claim 11 wherein the alkaline earth metal ions contribute less than about 50 meq./100 g to the ion exchange capacity of the catalyst.

14. The catalyst of claim 11 further comprising free alkaline earth metal ions or alkali metal ions in a proportion of less than about 5 meq./100 g of the catalyst.

15. The catalyst of claim 11 further comprising about 15 to about 55 percent by weight silicic acid.

16. The catalyst of claim 11 wherein the acid-activated clay mineral has a total acidity of more than about 15 mg of KOH/g.

17. The catalyst of claim 11 wherein the acid-activated clay mineral is formed into particles with diameters greater than about 0.1 mm.

18. A process for the preparation of a catalyst for removing olefins from aromatic compounds or mixtures of aromatic compounds comprising treating an acid-activated smectite clay starting material with an aluminum salt solution, wherein the salt solution comprises $Al^{3+}$ ions in a concentration of at least about 5 meq./100 g of the catalyst.

19. The process of claim 18 further comprising treating the acid-activated smectite starting material with $Al^{3+}$ ions in a molar excess of about 1 to about 5 times the ion exchange capacity of the acid-activated smectite to form a catalyst precursor and washing said catalyst precursor.

20. The process of claim 19 further comprising forming the washed catalyst precursor into particles with a diameter greater than about 0.1 mm.

21. A process for removal of olefins from aromatic compounds or mixtures of aromatic compounds comprising feeding the aromatic compounds or mixtures of aromatic compounds across a bed of catalyst, wherein the catalyst comprises an acid-activated clay mineral treated with a salt solution comprising $Al^{3+}$ ions in a concentration of at least about 5 meq./100 g of the catalyst, wherein the acid-activated clay mineral is formed into particles having a specific surface area from approximately 50 to about 250 m²/g.

22. The process of claim 21 wherein the acid-activated clay mineral further comprises alkali metal ions and alkaline earth metal ions, wherein the alkali metal ions contribute less than about 7.0 meq./100 g to the ion exchange capacity and the alkaline earth metal ions contribute less than about 50 meq./100 g to the ion exchange capacity of the catalyst.

23. The process of claim 21 wherein the acid-activated clay mineral further comprises free alkaline earth metal ions or alkali metal ions in a concentration of less than about 5 meq./100 g of the catalyst.

24. The process of claim 21 wherein the acid-activated clay mineral further comprises about 15 to about 55 percent by weight silicic acid.

25. A catalyst for removing olefins from aromatic compounds or mixtures of aromatic compounds comprising an acid-activated clay mineral comprising exchangeable $Al^{3+}$ ions, wherein the exchangeable ions comprise at least about 10 to 60 meq./100 g of $Al^{3+}$ ions.

* * * * *